(12) United States Patent
Alessi et al.

(10) Patent No.: US 7,536,045 B2
(45) Date of Patent: May 19, 2009

(54) METHOD FOR THE ANALYSIS OF ARRAY IMAGES AND DEVICE

(75) Inventors: Enrico Alessi, Catania (IT); Giovanni Cuce, Gravina di Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 905 days.

(21) Appl. No.: 10/716,373

(22) Filed: Nov. 18, 2003

(65) Prior Publication Data

US 2004/0151383 A1 Aug. 5, 2004

(30) Foreign Application Priority Data

Nov. 22, 2002 (IT) .......................... VA2002A0060

(51) Int. Cl.
*G06K 9/00* (2006.01)
*G06K 9/64* (2006.01)

(52) U.S. Cl. ....................... 382/129; 382/224

(58) Field of Classification Search .......... 382/128–133
See application file for complete search history.

(56) References Cited

U.S. PATENT DOCUMENTS 5,764,792 A * 6/1998 Kennealy ..................... 382/133
6,901,168 B1 * 5/2005 Gardes et al. ................ 382/203
7,130,458 B2 * 10/2006 Bartell ........................ 382/128

FOREIGN PATENT DOCUMENTS

EP  IT- 1 182 602  2/2002

OTHER PUBLICATIONS

Unsupervised technique for robust target separation and analysis of DNA microarray spots through adaptive pixel clustering Bioinformatics vol. 18 No. 5 2002 pp. 747-756, by Daniel Bozinov and Jorg Rahnenfuhrer.*
Analysis of cDNA microarray images; Briefings in Bioinformatics 2001 2(4):341-349; doi:10.1093/bib/2.4.341; By Yee Hwa Yang, Michael J. Buckley, and Terence P. Speed.*
Yang, Y. H., Buckley, M. J., Dudoit, S. and Speed, T. P. (2002). Comparison of methods for image analysis on cDNA microarray data. J. Comput. Graph. Statist. 11 108-136.*
Alessi, et al., "A New Clustering Based System for Automated Object Recognition", Dipartimento Elettrico, Elettronico e Sistemistico, Dipartimento di Matematica, Università di Cantania, Catania, Italy. (date unknown).
Siddiqui, et al, "Mathematical Morphology applied to Spot Segmentation and Quantification of Gene Microarray Images," Conference Record of the 36th Asilomar Conference on Signals, Systems & Computers; Pacific Groove, CA, Nov. 3-6, 2002, asilomar Conference on Signals, Systems and Computers, New York, NY IEEE, US, vol. 1 of 2, Conf. 36, Nov. 3, 2002, pp. 926-930, XP010638337; ISBN: 0-7803-7576-9.

(Continued)

*Primary Examiner*—Jingge Wu
*Assistant Examiner*—Hadi Akhavannik
(74) *Attorney, Agent, or Firm*—Gardere Wynne Sewell LLP

(57) ABSTRACT

A method of image analysis applicable to the analysis of arrays, such as DNA or protein microarrays. In the method the luminous spots of the array are filtered and isolated without any intervention of the operator by using a technique of morphological filtering. The spots thus isolated are subsequently analyzed by a fuzzy logic algorithm.

16 Claims, 15 Drawing Sheets

OTHER PUBLICATIONS

Zhou, et al., "GLEAMS: A Novel Approach to High Throughput Genetic Micro-Array Image Capture and Analysis," Proceedings of the SPIE, SPIE, Bellingham VA, US; vol. 4266, Jan. 21, 2001, pp. 13-23; XP001172893; ISSN: 0277-786X.

* cited by examiner

| Name | Structuring set | Direction |
|---|---|---|
| OpeningD1 | | $d_1$ |
| OpeningD2 | | $d_2$ |
| OpeningX | | x |
| OpeningY | | y |
FIG. 4
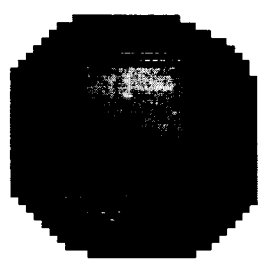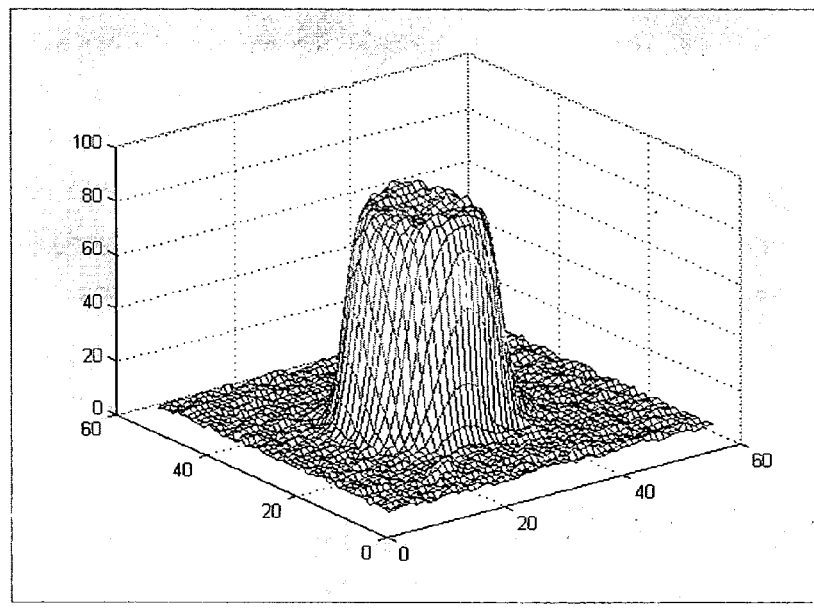
FIG. 5

Area

Background

Area

METHOD FOR THE ANALYSIS OF ARRAY IMAGES AND DEVICE

PRIORITY CLAIM

This application claims priority to IT VA2002A000060 filed on Nov. 22, 2002, the disclosure of which is hereby incorporated by reference.

FIELD OF THE INVENTION

This invention relates to methods for analyzing images. In particular, it relates to a method and device for the analysis of images acquired from arrays employing a technique of morphological filtering.

BACKGROUND OF THE INVENTION

Processing techniques for analyzing images are useful in various areas, for example, the identification of objects photographed from a satellite or telescope and the consequent extraction of the relative pixels from the rest of the photographic image. The analysis of images is of crucial importance even in medicine. For example, DNA analysis based on the use of so-called "DNA chips" has been developed and is of increasing importance in the health industry. Indeed, this market is expected to grow to more than $600 million by 2005. A crucial component of DNA chip use is the analysis of the images produced by the chip.

According to one method developed at Stanford University, DNA chips are realized by placing fragments of nucleic acid or "probes" by robotized deposition in a matrix-like arrangement at defined areas on a surface, such as a microscope slide. Probes can also be synthesized in situ, directly on the slide or other surface. The matrix of spots is called an "array" or "microarray," and can contain hundreds to hundreds of thousands of specific probes for diagnostic, drug discovery, or toxicology uses. In the future, it is expected that even "nanoarrays" will come into general use as the sensitivity of detection increases and as technology is developed to print such fine arrays.

In diagnostic uses, for example, a sample is taken from the blood, urine, saliva or other tissue of the individual. Very often the DNA in the sample is amplified and labeled with one or more fluorescent dyes. If mRNA is to be studied, it is first copied to cDNA, and then amplified and labeled. Changes in the amount or sequence of particular nucleic acids in the sample can be detected on the basis of hybridization to the probes on the DNA chip. This is possible because conditions can be established to allow only perfectly complementary nucleic acids to hybridize to the probes on the chip. When the chip is activated by shining light on it, those probes or "spots" that contain a hybridized labeled sample will fluoresce and can be detected. Thus, hybridization is detected by detecting a fluorescent label at the individual spots of the array.

In one particular application, a reference DNA and a test DNA are both labeled with different dyes and analyzed simultaneously. For example, the reference DNA is labeled with a red dye (CY3) and the test DNA with a green dye (CY5). Thereafter, both samples are applied to a DNA chip and allowed to hybridize with their complementary probes on the DNA chip. This, dual-label analysis can be used in many applications, including the detection of mutations or particular alleles in an individual, or in monitoring the expression of genes in healthy and diseased tissue types. Indeed, multi-label applications can be and are used in DNA chip applications, limited only by the ability to collect and analyze different wavelength signals.

By using a confocal scanner, the DNA chip is thereafter subjected to two (or more) different scans with wavelengths appropriate to the dyes employed. The two images that are obtained are processed by a special computer program capable of analyzing, on the basis of the intensity of fluorescence, whether a labeled nucleic acid is present or not. The luminance (grey-level) of the pixels of the luminous spots in the two images is proportional to the number of dye molecules at the corresponding location of the array. By comparing the red and green images (matching) it is possible to identify the samples that contain sequences complementary to the probe sequences.

It should be noted that any matching analysis is carried out only after the luminance or grey-level of the signal pixels for each luminous spot for both channels (images) has been normalized with respect to the respective luminance (grey level) of the background pixels. Moreover, a further normalization operation is necessary between the images obtained from the two channels (different scanning wavelengths) in view of the fact that the respective mean luminance or grey-level of corresponding spots of the two images changes depending on the dye used.

The processing of the images acquired from an array is complicated by the fact that the data is subject to a number of sources of error. For example, sample nucleic acids maybe differentially amplified, differentially labeled, or hybridize to differing degrees at the particular conditions employed. The array spots themselves may also vary in quality. There may also be errors in data acquisition, for example due to noise. Finally, there may be errors introduced by operator intervention or by imprecision of the instruments used. The fact that the intervention of the operator for analyzing array images is necessary detracts from the reproducibility of the results of the analysis. As a consequence, any matching operation could be inadvertently vitiated ab initio by human error, which may lead to erroneous conclusions.

FIG. 1 shows 48 luminous spots of an image of good quality acquired from an array that has been hybridized to a test DNA labeled with a single dye. It is possible to note some typical characteristics of all array images, indicated on the filtered image of FIG. 2. The luminous spots on the left side of the figure are DNA probes that are relatively neatly rendered in the filtered image. These spots are small, substantially circular, and localized on the darker background. There is also the occasional localized noise (see the two stripes and random small bright pixels) that depend on the fabrication or hybridization process and is generally unforeseeable. Such noise causes variations of the grey level in the darker background areas and within the luminous spots that represent the useful signal.

In general, the analysis of array images contemplates the following steps:
  i) array localization, which comprises determining the location and shape of the luminous spots;
  ii) spot extraction, which comprises isolating single luminous spots;
  iii) intra-spot segmentation, which comprises examining each spot by distinguishing the signal pixels from the background and noise pixels; and
  iv) spot quality measurement, which comprises deriving characteristic parameters of the spots and indexes indicative of the quality.

Array localization is the step that according to present practices requires significant intervention by the operator, who must center each single luminous spot within a respective mesh of a micro-grid. This operation is rather laborious considering that typically the acquired images may contain 10,000 or more spots, distributed on several grids. At the present state of the art, this operation is semi-automatic. The array localization techniques allow to automatically position the grid, but a final trimming by the operator to correct errors of execution of the positioning algorithm is always required. This human intervention may be required for precise tuning, but may also introduce non-negligible human errors and decrease the inter-experiment comparability of the results.

Once the grid is correctly positioned, a binary map that defines the boundaries of the luminous spots on the background is generated. This map is used for isolating the luminous spots that are thereafter examined with a segmentation technique.

The segmentation techniques most widely known for discriminating the signal pixels from the background pixels within a luminous spot are listed herein:

i) Pure Spatial Segmentation;
ii) Pure Intensity-based Segmentation;
iii) Mixed Spatial/Intensity Segmentation;
iv) Mixed Spatial/Statistics Segmentation; and
v) Mixed Spatial, Intensity, Statistics & Morphology Segmentation.

The "Pure Spatial Segmentation" technique rests on the assumption that all the pixels within a circle (any geometric shape may be used, but for simplicity we refer to a substantially circular spot shape) of a size that is preselected by the operator are signal pixels, while all pixels contained in a neighboring area, of shape and distance from the perimeter of the preselected signal area of which are selected by the operator, are background pixels. In this case, discrimination of the pixels is made only by taking into consideration their location.

The technique of "Pure Intensity-based Segmentation" considers only the pixels of the area containing the spot, and on the basis of the grey level of the internal pixels discriminates signal pixels from background pixels. In this case, discrimination of the pixels is made only by taking into consideration their grey level.

According to the technique of "Mixed Spatial/Intensity Segmentation" the discriminant among signal pixels and background pixels is the luminance, but in two different regions, the circular spot area and the surrounding area. This technique rests on both a spatial and grey level characterization of the pixels.

According to the technique of "Mixed Spatial/Statistics Segmentation" a threshold (level of grey) that discriminates a signal pixel from a background pixel is calculated by statistic methods. The luminance of the pixels within the circular spot area is compared with such a threshold.

The technique of "Mixed Spatial, Intensity, Statistics & Morphology Segmentation" is based on a statistical prior knowledge obtained by a local analysis of the spots, on the luminance distribution and on the morphological characteristics of the spots.

The main characteristics considered as indexes of quality and parameters of comparison among spots are the median luminance values (grey levels) of the signal pixels and of the background pixels, respectively. In general, according to the known methods, eventual morphological characteristics of the spots that may be important in the final phase of validation of the results are not considered.

SUMMARY OF THE INVENTION

By "Array" herein is meant any matrix of biological probes, such as DNA, RNA, peptides, antibodies, drugs and the like, wherein the probes are arranged in known locations, typically on a surface. The term array includes microarrays, nanoarrays and the like.

The present invention is generally directed to a method of array analysis, wherein the isolation of the spots is automatically performed, thus eliminating any error-prone human intervention steps and in addition simplifying and reducing data processing time. According to this new approach, the luminous spots are filtered and isolated without any intervention of the operator by using a technique of morphological filtering. The spots thus isolated are subsequently analyzed by a fuzzy logic algorithm.

More precisely, one embodiment of this invention is a method of analysis of images detected from an array in a form of one or more luminous spots on a background comprising:

i) determining shapes and relative locations of said spots on the area of the array image (array localization) generating a binary map of pixels defining boundaries of the luminous spots on the background;
ii) isolating each spot by an extraction step (spot extraction) using said binary map;
iii) analyzing the spots by a segmentation step (intra-spot segmentation) identifying by a preset criteria the pixels belonging to a same cluster of pixels; and
iv) determining relative characteristic parameters and indexes of quality for each spot.

According to one aspect of this invention, intervention of the operator is no longer required for isolating the single spots because the binary map is generated with a technique of morphological filtering including:

i) filtering an array image with at least a morphological filter generating a corresponding "marker" image of the background;
ii) reconstructing the background by performing a reconstruction operation on the "marker" image, generating a corresponding reconstructed background image;
iii) generating a filtered image of the luminance of the background by performing a top-hat operation on the reconstructed image and on the array image; and
iv) generating said binary map by a thresholding operation on the filtered image of the background luminance.

The morphological filtering is implemented via hardware by a device of analysis of array images configured according to an architecture of neural cellular network.

A further embodiment of this invention is a method of identifying the pixels of an image belonging to a same object on a background comprising scanning the pixels of the image, and calculating a characteristic value for each pixel with a fuzzy logic algorithm, having as antecedents:

i) the gray level of the currently processed pixel;
ii) the distance between the gray level of the pixel and the mean value of the gray level of respective background pixels; and
iii) the square of the above-defined distance; and the method comprising calculating the mean value of the gray level of background pixels and discriminating the scanned pixels as belonging to a same object if their characteristic values exceeds a pre-established threshold. The latter method is implemented via hardware by a fuzzy logic system.

BRIEF DESCRIPTION OF THE DRAWINGS

The different aspects and advantages of this invention will become even more clear through the following detailed description, making reference to the attached drawings, wherein:

FIG. 4 shows the scheme of morphological filtering to be carried out on an image as detected by an array, according to a preferred embodiment of the method of analysis of this invention;

FIG. 5 shows a luminous spot to be filtered with the respective map of grey levels;

DESCRIPTION OF SEVERAL EMBODIMENTS OF THE INVENTION

Figure 1:
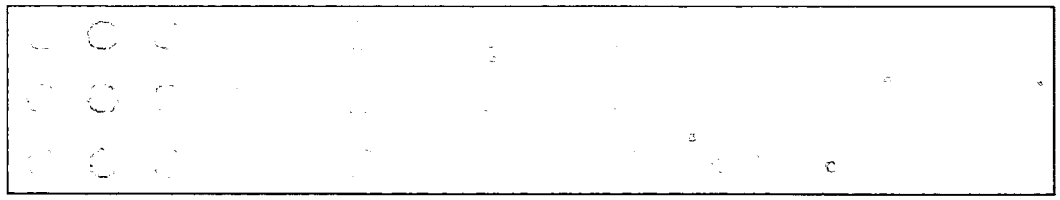
FIG. 1 shows an image detected from an array.
Figure 2:
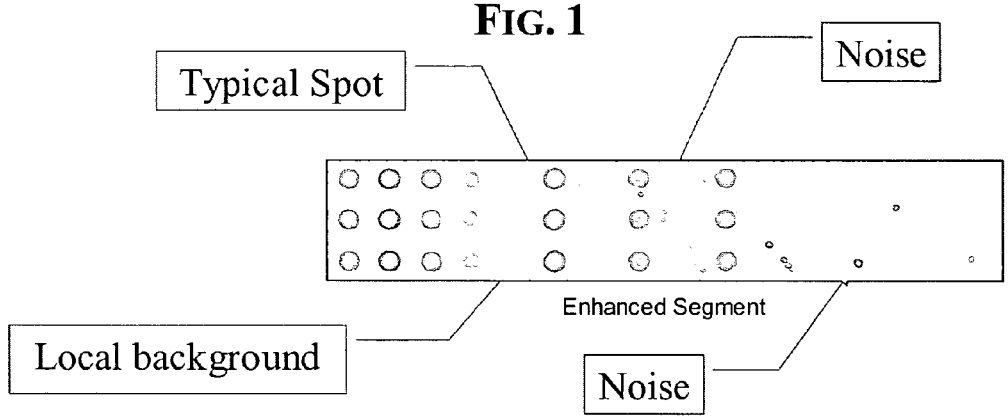
FIG. 2 shows the image of FIG. 1 after filtering.
Figure 3:
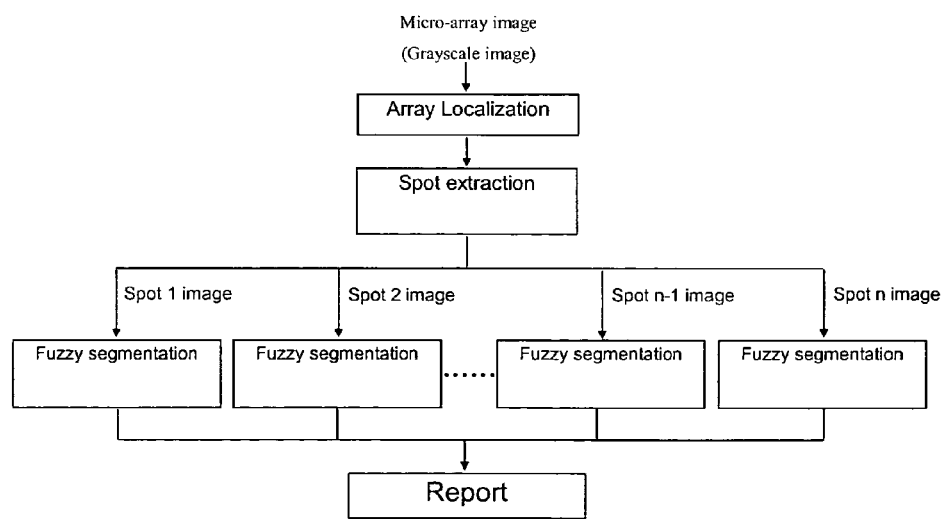
FIG. 3 is a block diagram of a preferred embodiment of the method of analyzing array images according to this invention.
Figure 6:
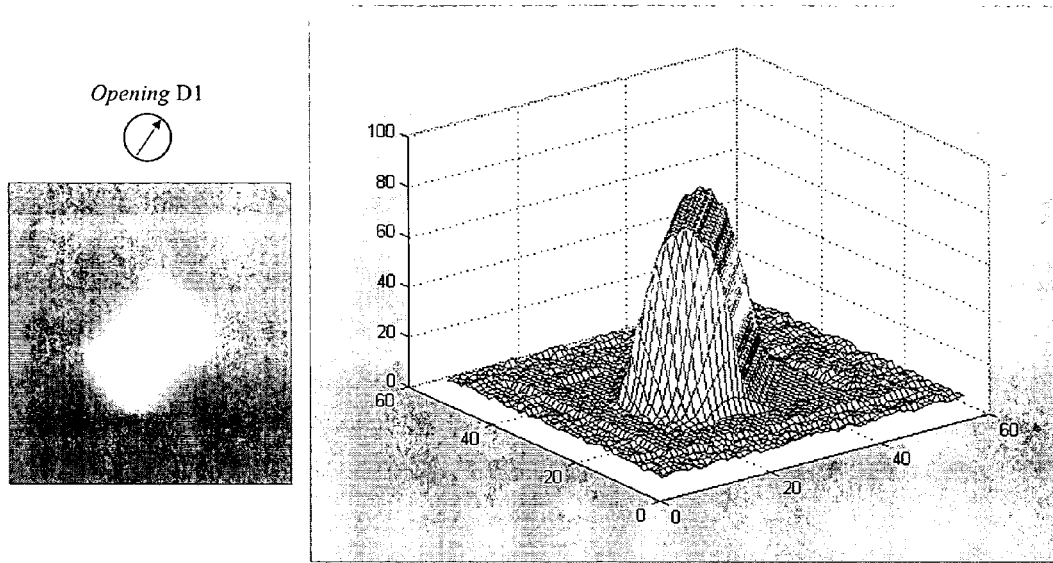
FIGS. 6 to 9 show spots with respective maps of luminance levels, obtained by successive filterings of the spot of FIG. 5 using the morphological filters indicated in FIG. 4.
Figure 7:
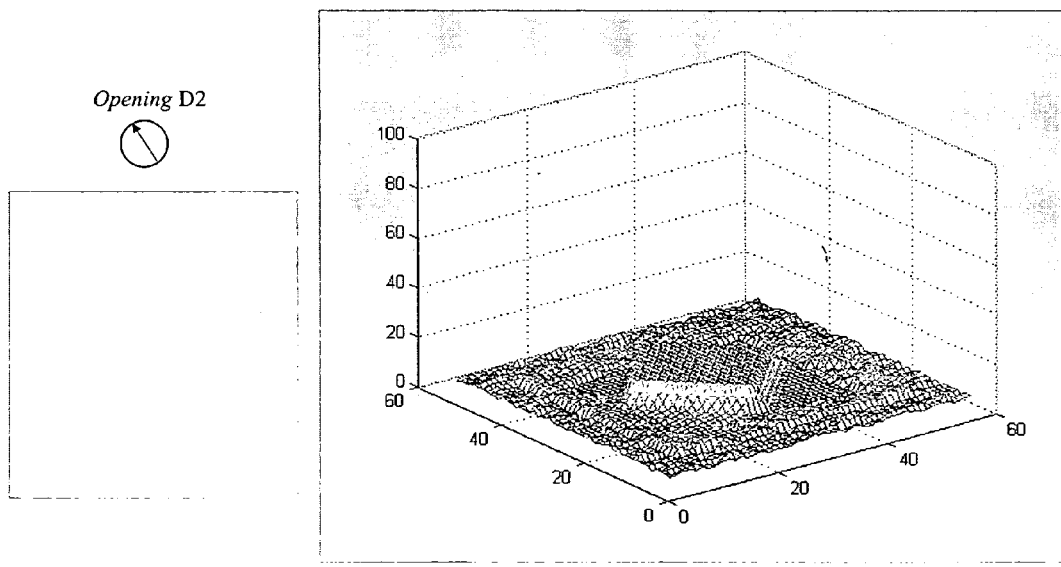
Figure 8:
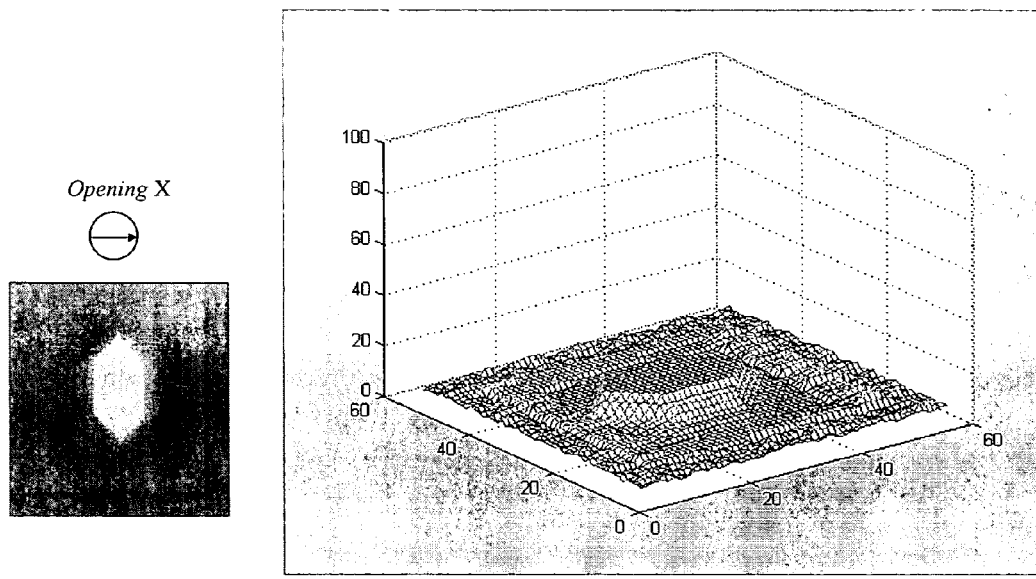

According to one feature of the invention for the analysis of array images, the array process for localization (see, FIG. 3) is performed by morphological filtering operations.

In consideration of the fact that the shapes of the luminous spots on the background of typical arrays can be approximated to disks having a diameter that is not larger than a certain length, and therefore belonging to a class of geometrical figures substantially symmetrical about their center, morphological filters of appropriate directional apertures may be defined.

Preferably, four morphological filters in cascade are used, each defining a respective aperture based on a structure set in the form of slits of length not greater than the maximum diameter of the luminous spot and oriented along the fundamental Cartesian directions (X, Y) and along the two main diagonals ($D_1$, $D_2$), as schematically illustrated in FIG. 4.

Alternatively, it is also possible to use morphological filters defined differently from the ones of FIG. 4 for example a single morphological filter the aperture of which is the result of the composition of four segments (slits) intersecting at the same point which divide the plane in eight equal angles. From comparative tests it has been found that using such an alternative morphological filter the results were generally worse than when employing four distinct mono-segment morphological filters in cascade.

Figure 9:
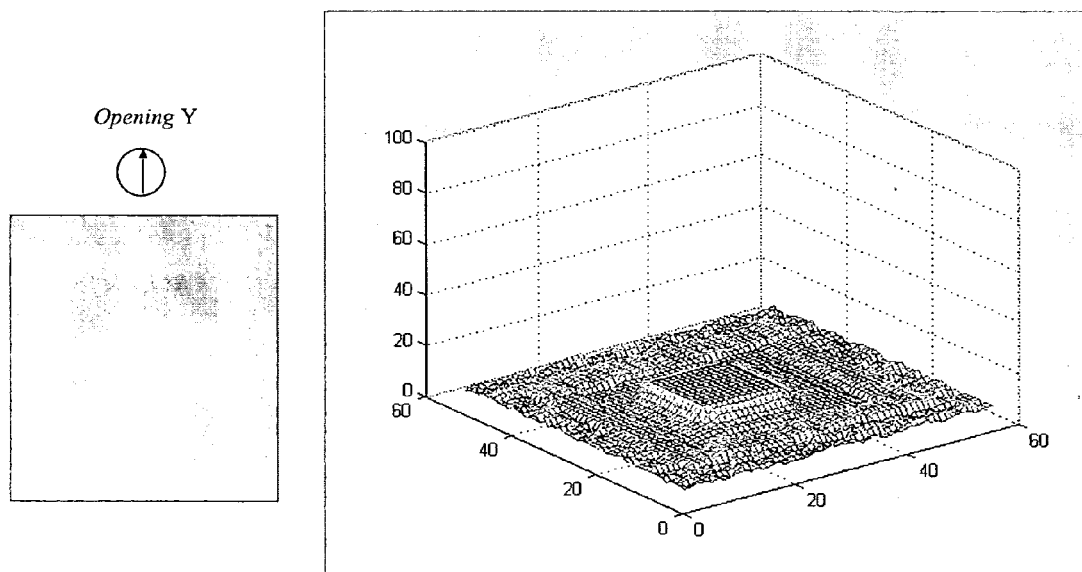

By filtering the spot of FIG. 5 in succession with the morphological filters of FIG. 4, the spots shown in F*igure* from 6 to 9, are obtained. By filtering the spots with the four distinct morphological filters the so-called "marker" image of the background, as represented in FIG. 9, is obtained.

Figure 10:
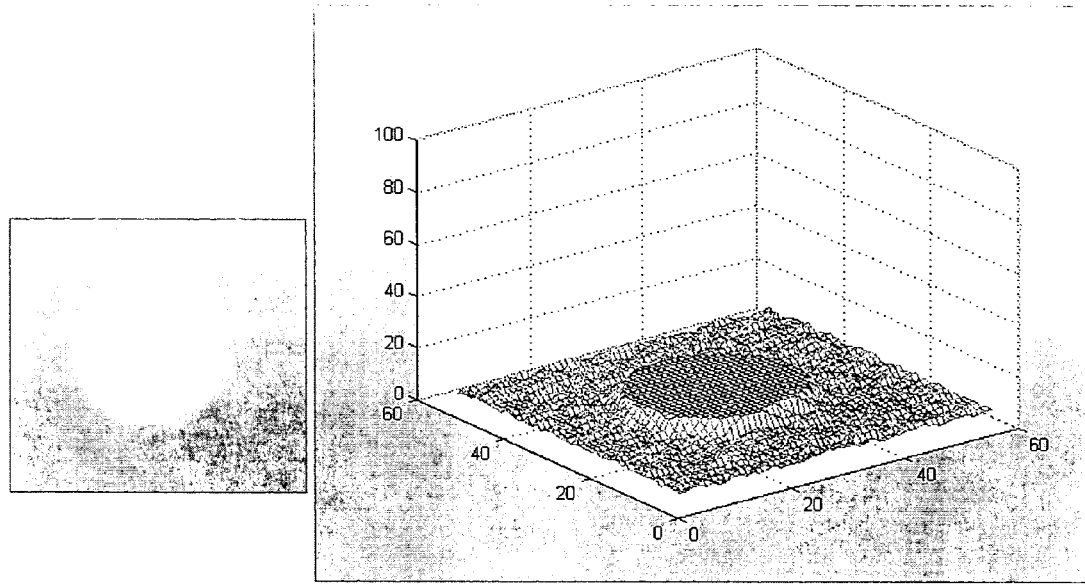
FIG. 10 shows a spot with relative map of luminance levels, of a background image obtained by performing a reconstruction operation on the spot of FIG. 9.

Successively, a reconstruction operation on the "marker" image is carried out for obtaining a reconstructed background image represented by a spot as the one depicted in FIG. 10.

Figure 11:
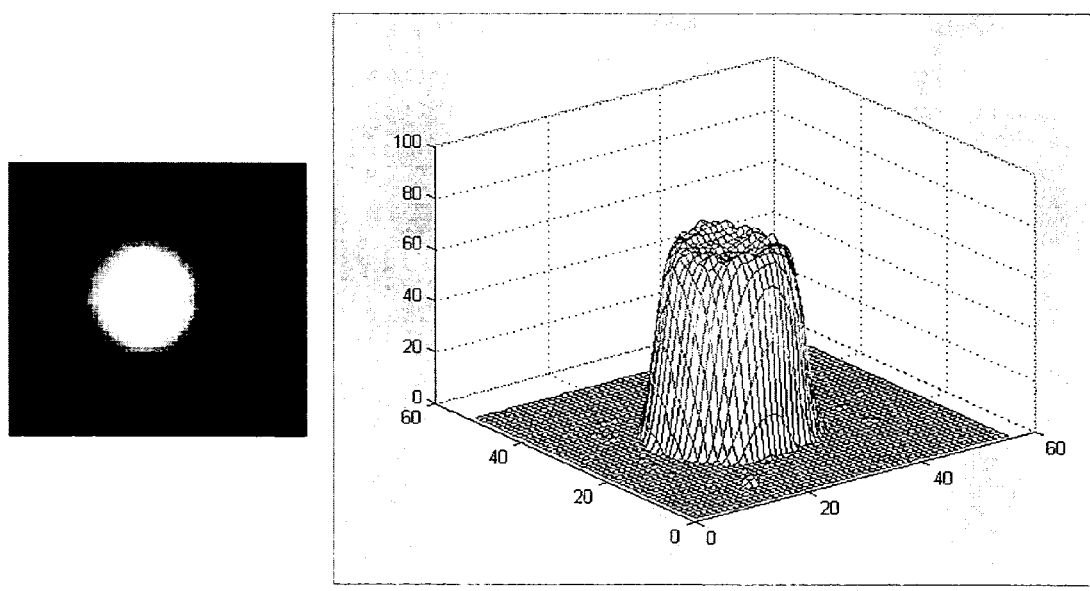
FIG. 11 shows a spot filtered from noise, with its relative map of luminance levels, obtained by carrying out a top-hat operation of the spots of FIGS. 5 and 10.

A top-hat transformation operation is then performed using the original image and the reconstructed background image thus obtaining an image that has been filtered from the background luminosity, which is represented by a spot as the one depicted in FIG. 11, corresponding to the original spot of FIG. 5 wherein the background luminosity has been practically eliminated.

Finally, a binary map is generated by a thresholding operation, comprising substantially of comparing with a threshold level the map of grey levels of the image that is obtained from the top-hat operation: if the grey level of a pixel exceeds the established threshold, a corresponding pixel of the binary map is generated with an active logic value (1), otherwise a pixel of the binary map of null logic value (0) is generated.

Because of edge effects, but also because often pixels pertaining to background or noise are completely eliminated, the reconstruction operation does not permit to obtain the same original image of the spots on the background.

The top-hat operation thus provides an image in grey tonalities wherein besides the spots an impulsive noise is also present. That is, even the binary map is corrupted by noise. However, the distribution of the impulsive noise corrupting the binary map is such to permit an easy removal thereof by carrying out two erosion operations, using as a structuring set two circular masks of different radii.

For reasons that will become more evident later in this description, it is desirable to obtain a binary map that includes beside the luminous spot also a neighboring background area of sufficient width to permit to calculate with a good reliability the local background luminosity. To this end, according to an embodiment of the method of this invention, a dilation operation is performed using a circular mask of diameter larger than the diameter of the spot. Such a dilation operation permits one to compensate for the undesirable effects of the erosion operations, which substantially result in a restriction (on the binary map) of the zone of the luminous spot such to exclude the possibility that it may contain only background and/or noise pixels.

Figure 12:
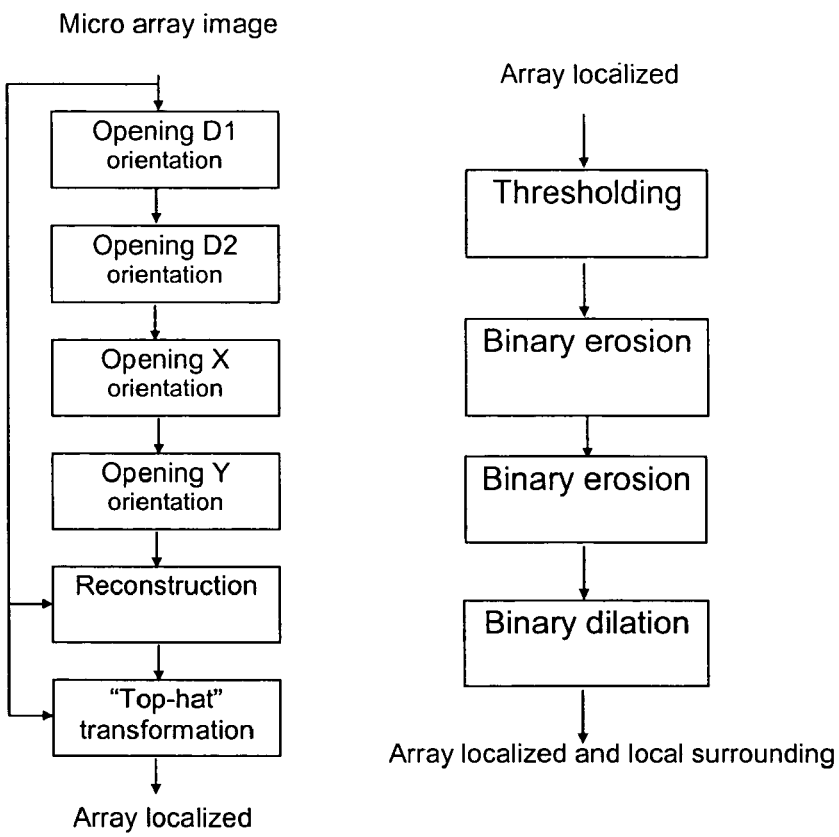
FIG. 12 is a flow chart of the array localization phase according to a preferred embodiment of the method of analysis of images of this invention.

A flow chart that summarizes the process steps of the array localization operation (of FIG. 3), according to the analysis method of this invention, is depicted in FIG. 12.

The array localization operation may be conveniently carried out by using an array localization system organized according to a neural cellular network architecture of the type described in EP-A-1 182 602, in the name of the same applicant, the disclosure of which is hereby incorporated by reference.

Figure 13:
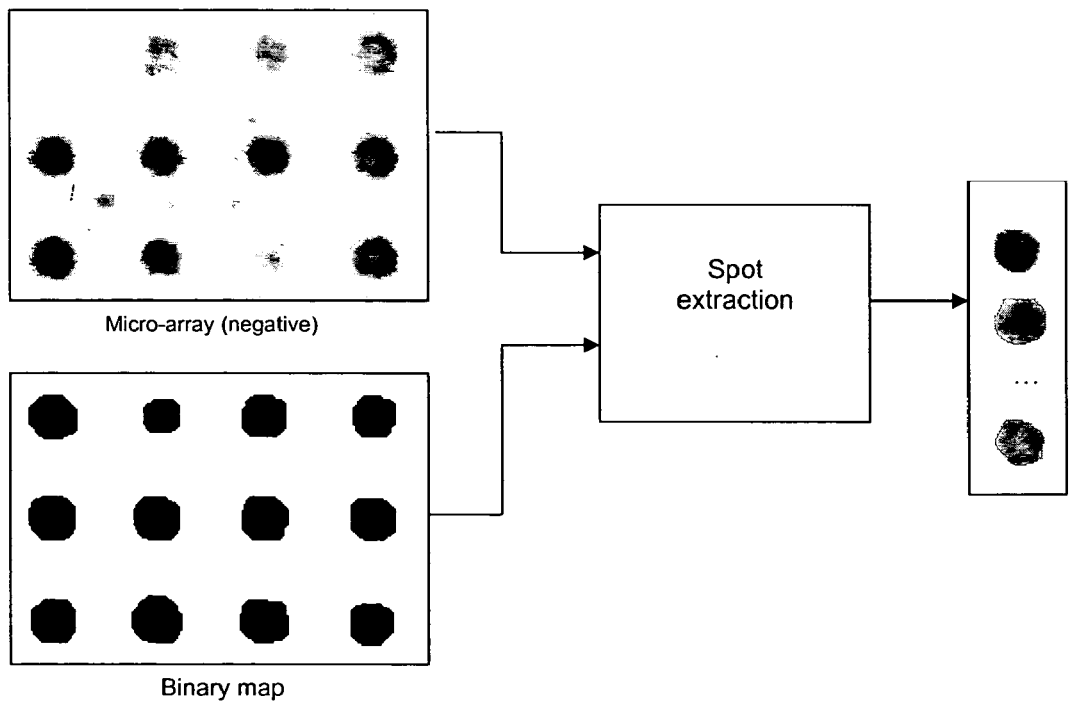
FIG. 13 schematically illustrates the spot extraction operation of the method of analysis of images of this invention.

The image obtained by the array localization process is a binary logic map, as depicted in FIG. 13, containing the silhouette of each spot. The black pixels have an active logic value (1) and indicate that they correspond to signal pixels of a spot, while the white pixels have a null logic value (0) indicating that they correspond to background or noise pixels of the image.

Therefore, to extract the spots (see, FIG. 3), it is possible to use any known algorithm of identification of clusters (clustering) in images, based on the properties of the pixels of the image.

An algorithm of identification of clusters particularly suitable for use with the method of the invention, is described in the document "A NEW CLUSTERING BASED SYSTEM FOR AUTOMATED OBJECT RECOGNITION" SOCO'98—University of Catania, by Enrico Alessi, Salvatore Coco, Giuseppe Pappalardo, Giacomo Capizzi. The algorithm uses the Euclidean distance as metric and a clustering threshold condition for identifying pixels belonging to the same cluster.

Such an algorithm, which will be described in more detail later in this description, may be useful even for carrying out operations other than spot extraction in array images. The algorithm is particularly convenient because it works regardless of the predicate specified by the user for discriminating signal pixels from background pixels, without modifying the succession of process steps. Moreover, the algorithm permits also to use predicates of "soft computing" techniques and has the advantage of not requiring the intervention of the analyst. Moreover, the algorithm does not require any initial condition (seed of the algorithm), differently from many other algorithms that generate different results depending on the seed originally chosen.

Figure 14:
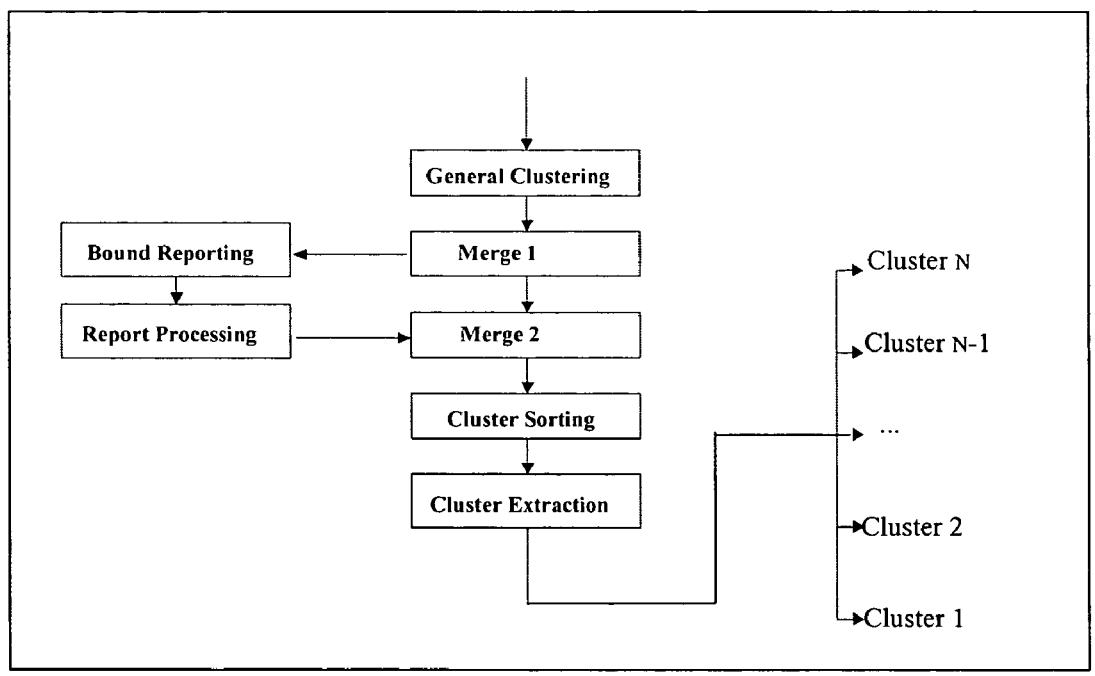
FIG. 14 is a flow chart of an algorithm of identification of clusters (clustering) in an image.

A flow chart of the cluster identification algorithm employed for performing the spot extraction operation (of FIG. 3) according to the invention is illustrated in FIG. 14.

The first step GENERAL CLUSTERING comprises scanning by column (or by row) the pixels of the filtered image and grouping in elementary clusters the pixels of the same column (row) successively scanned, that is the adjacent pixels of the same column (row) that satisfy a certain criterion. Each elementary cluster is defined by an identification number INDEX, by a column (row) number y and by the minimum and maximum coordinates: $x_{min}$ and $x_{max}$, respectively, of the cluster on the y column (row).

The particular criterion used for the spot extraction operation comprises in grouping in the same elementary cluster the pixels belonging to the same column (row) that are successively scanned and that correspond to pixels of the binary map having the same logic value.

Figure 15:
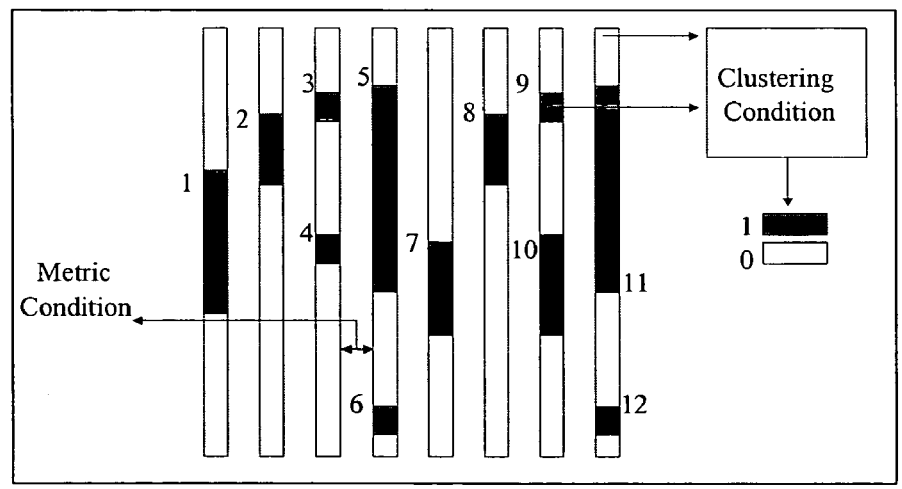
FIGS. 15 to 20 illustrate the functioning of the algorithm of identification of cluster (clustering) described in FIG. 14.

In order to better understand the functioning of the algorithm, a brief general description will follow, with reference to FIGS. 15 to 20. FIG. 15 shows columns of pixels of an image already grouped in elementary clusters following the execution of a general clustering operation carried out according to a certain criterion. For example, such a criterion may be determined by a predicate based on soft computing or it may be a criterion based on a threshold. The identification number of the elementary clusters is shown at the left of each cluster.

The pixels of the same elementary cluster are represented as pixels of a binary image having an active logic value (1), while the background or noise pixels are represented as pixels having a null logic value (0).

Figure 16:
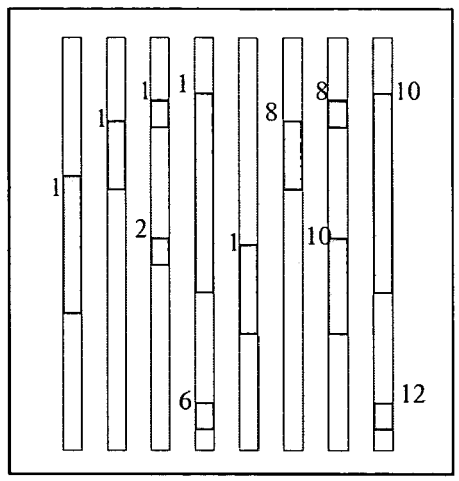

The elementary clusters are subjected to a first merging operation MERGE1, performed in two steps: firstly for each elementary cluster c in a certain column (row) thereof, a set of elementary clusters S in the column (row) immediately preceding said certain column (row) that are adjacent to said elementary cluster c are identified; thereafter within this set of neighboring clusters S a "winner" cluster w is identified as the one having the largest number of boundary pixels with the cluster c and its identification number is made equal to that of the cluster c. The result of the MERGE1 operation on the binary image of FIG. 15, is shown in FIG. 16.

The other clusters of the S set, different from the winner cluster, are identified as "loser" clusters and to them is assigned a respective triplet comprising their identification number, the identification number of relative winner cluster and the number of the column to which they belong (BOUND REPORTING, REPORT PROCESSING).

Figure 17:
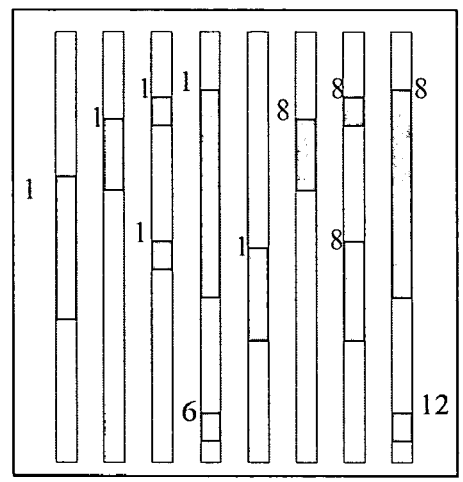

The identification numbers of the loser clusters are changed in the identification numbers of the respective winner clusters by the operation MERGE2, the result of which is shown in FIG. 17. At this point, the elementary cluster belonging to a same object are identified by the same identification number.

Figure 18:
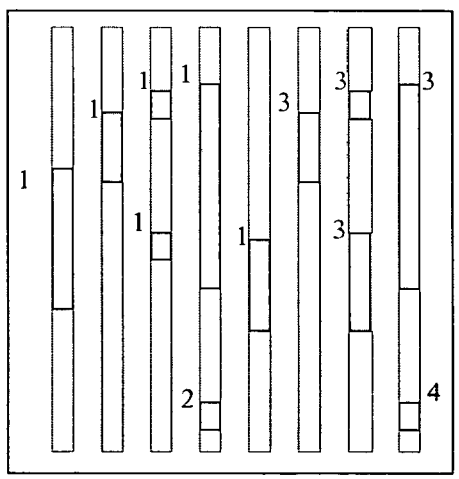

For simplicity's sake, consecutive identification numbers may be assigned to the different objects as recognized at the conclusion of the grouping performed during the operation of CLUSTER SORTING, as depicted in FIG. 18.

Figure 19:
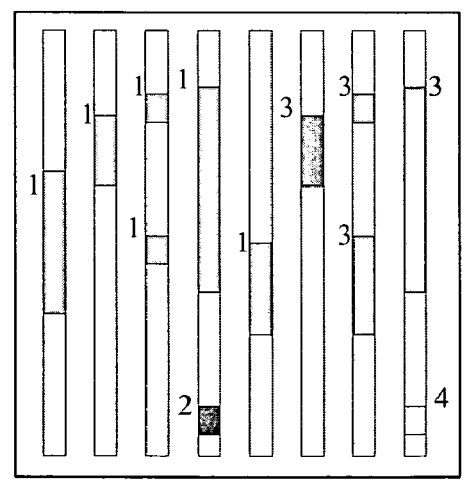
Figure 20:
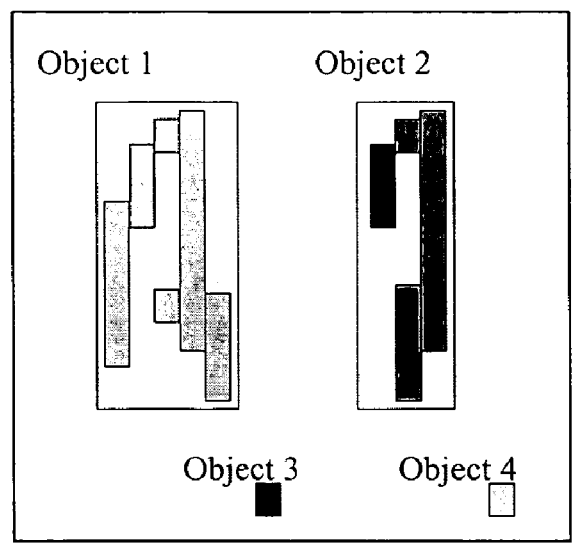

Finally, with the operation CLUSTER EXTRACTION, the pixels corresponding to elementary clusters having the same identification number are extracted from the original image of FIG. 19, which is associated to the binary image of FIG. 15, thus isolating the single objects represented therein, as shown in FIG. 20.

According to the method of analysis of array images of this invention, by applying the above described algorithm to the binary map obtained from the array localization operation and to the relative filtered image as previously described, the single luminous spots are reliably isolated without any intervention of the analyst, as illustrated in Figure from 21 to 25.

Figure 21:
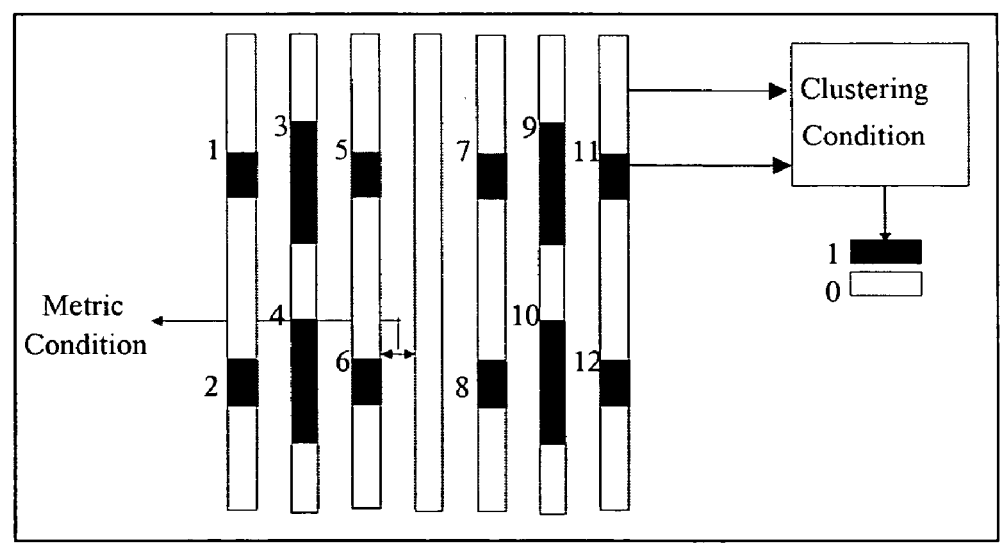
FIGS. 21 to 25 illustrate the algorithm of cluster identification (clustering) described in FIG. 14 for carrying out the spot extraction operation on an image detected by an array.

A styled form representation of a binary map is shown in FIG. 21.

Figure 22:
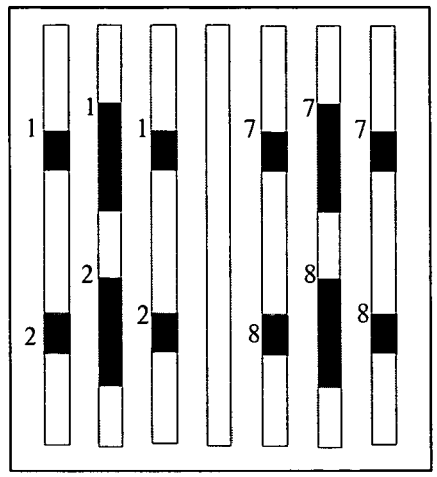
Figure 23:
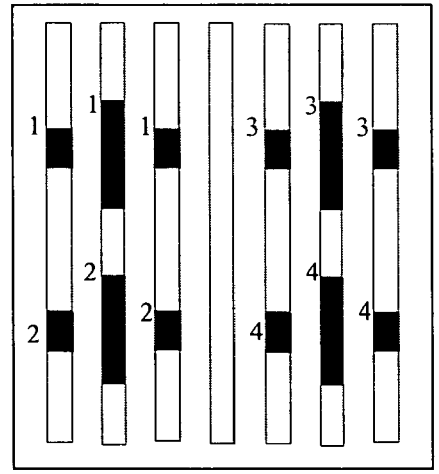

FIG. 22 shows the result of the MERGE1 operation (in the case of FIG. 21 the operation MERGE2 does not produce any change) and FIG. 23 shows the result of the CLUSTER SORTING operation.

Figure 24:
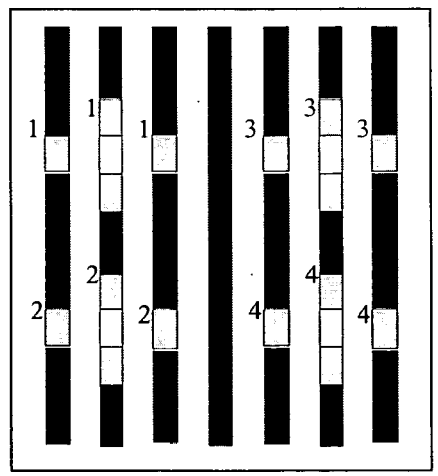
Figure 25:
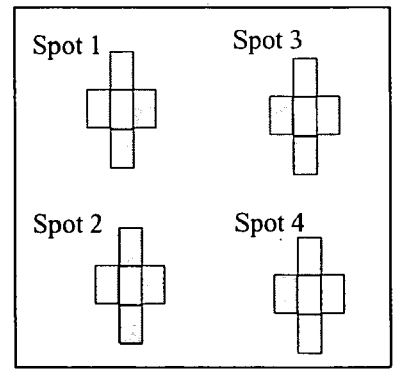

FIGS. 24 and 25, similarly to FIGS. 19 and 20 illustrate the spot extraction from an array detected image.

Figure 26:
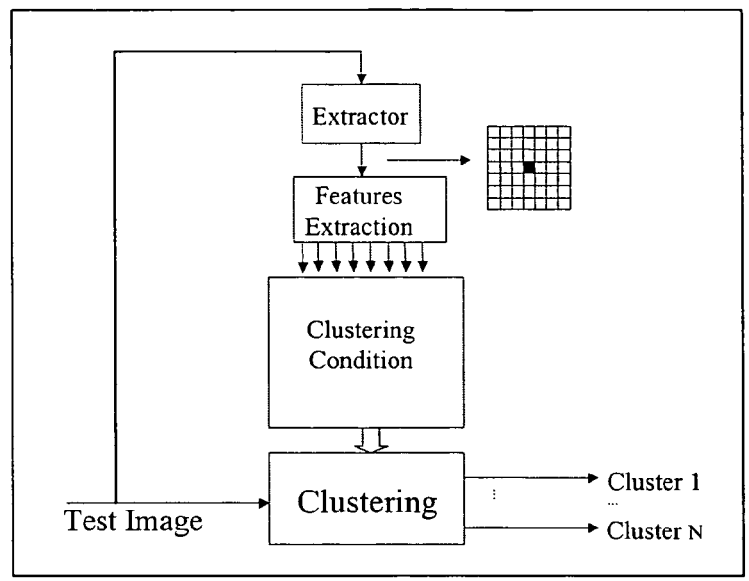
FIG. 26 illustrates a spot extraction system for luminous spots on a background in images detected by an array.

A possible spot extraction system for luminous spots on a background, of images acquired from an array, is shown in FIG. 26.

The system comprises a scanning subsystem EXTRACTOR of the pixels of an image, a subsystem of determination of elementary clusters (FEATURES EXTRACTION, CLUSTERING CONDITION) and a processing subsystem (CLUSTERING).

The block FEATURES EXTRACTIONS extracts from the scanned pixels the respective grey level and supplies this information to the cascaded block CLUSTERING CONDITION, which groups the pixels in elementary clusters.

Finally, the processing subsystem CLUSTERING of the elementary cluster outputs the pixels in clusters CLUSTER 1, . . . , CLUSTER N, representing the isolated luminous spots of the array image according to the extraction operation described above.

Thereafter, the luminous spots so isolated from the image are singularly processed through a segmentation operation (intra-spot segmentation), in order to identify objects represented therein.

The intra-spot segmentation operation comprises identifying pixels belonging to a same object by using a similarity criterion among pixels. Theoretically, it is possible to use various similarity criteria based on the luminance of the pixels and on other properties of pixels in the neighborhood of the currently evaluated pixel. Of course, the selection of the criteria must take into consideration the specific problem to be solved.

For example, should it be desired to extract all the objects defined by their recognized boundaries contained in an isolated spot of an array image and if the spot is free of noise, the extraction criterion could be based only on the value of the luminance gradient of a window of a size of 3×3 or 5×5 centered on the considered pixel. In case the spot is corrupted by the presence of noise, a simple predicate as the one mentioned above would not work and it would be necessary to use criteria based on other properties that are generally more burdensome from the point of view of computational complexity.

The human reasoning for identifying an object within an image is rather complex, based on numerous parameters and at times hardly definable from a mathematical point of view.

For this reason, in order to solve the most complex problems of identification, criteria defined by soft computing predicates are used as an alternative to criteria defined by threshold type predicate.

In particular, a neural predicate of the MLP (acronym for Multi Layer Perception) type and other types of predicates based on fuzzy logic may be used. Both types of predicates allow to overcome the problems that arise in situations that would require criteria hardly definable mathematically; moreover, they permit even a multicriteria decision taking and confer robustness to the system whenever objects must be individuated in images that are heavily corrupted by noise.

According to another important novel aspect of the analysis method of this invention, the operation of segmentation (intra-spot segmentation, in the case of an array image) is carried out by a fuzzy logic algorithm (see, FIG. 3), which may be defined by linguistic rules formulated by an expert or by starting from a learning file containing the patterns of the properties and the corresponding outputs in relation to the problem to be solved. The novel approach based on a fuzzy logic algorithm for performing a segmentation operation, besides being outstandingly effective in analyzing arrays images, may be used successfully for analyzing even other types of images.

In the case of array images, the shape of the spot of the binary map obtained by the array localization operation is larger than that of the real spot, in order to select together with the luminous spot also the surrounding background zone. The grey level of the background in the surrounding area around the isolated spot serves for calculating a normalization factor and therefore should be precisely determined.

The normalization factor is important because the grey levels of images obtained varies also with the type of dye used in the experiment. In order to compare (match) images obtained with different dyes, the grey level of the luminous spots must first be normalized with respect to the grey level of the background. The grey level of each pixel should be determined with equal precision, especially in presence of spots that may easily confound themselves with the local background.

It is important to remember that background pixels may be nested also among signal pixels within the spot itself. This renders the criteria usable for distinguishing signal pixels from background pixels within a spot generally complex and difficult to formalize. In order to obviate to this difficulty, a fuzzy logic criterion has been found to effectively distinguish signal pixels from background or noise pixels within a luminous spot. According to fuzzy logic criterion, the pixels of a spot are scanned and a characteristic value is calculated for each scanned pixel: if the characteristic value exceeds a preset threshold, then the pixel is regarded as belonging to a cluster (object) present in the spot. The choice of antecedents used in the fuzzy logic algorithm is done after having studied the histogram of the grey levels of the spot.

It has been found that each spot usually has either a three-modal or a bi-modal histogram, depending on whether the spot is or is not corrupted by noise. In particular, while the first and second mode correspond respectively to the background and to the signal, the third mode relates to noise. Thus, the following three antecedents for an effective fuzzy logic algorithm were chosen:

i) the grey level (luminance) of the pixel under scrutiny;
  ii) the distance ($\delta$) of the grey level of the pixel under scrutiny from the mean grey level of the background pixels; and
  iii) the square of the above defined distance ($\delta^2$).

The rules, shape and location of the membership functions are generated automatically by using a neural network.

Preferably, though not necessarily, within a spot two zones are preliminarily identified: a zone defined "true signal" containing signal pixels and a zone "false signal" containing noise and/or background pixels. For separating pixels of the spot in a zone containing signal pixels and a zone containing background and noise pixels, a fuzzy logic algorithm with the above described three antecedents, each having three membership functions, is used.

Typical reference spots are used for training a fuzzy system destined to implement the algorithm. Patterns of these "learning" spots are composed of a set of logic values: 1 or 0, depending on whether the corresponding pixel is a signal pixel or a background pixel.

Figure 27:
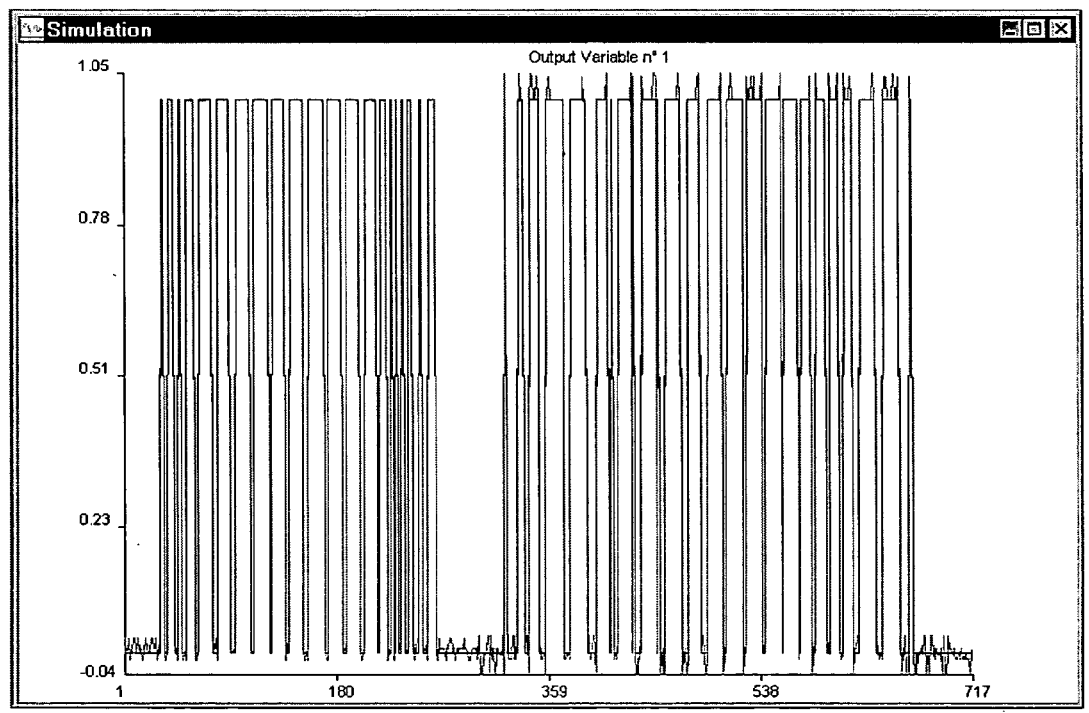
FIG. 27 is a simulation scheme of the fuzzy logic system used according to this invention, in correspondence of training patterns corresponding to two spots of different luminance levels.
Figure 28:
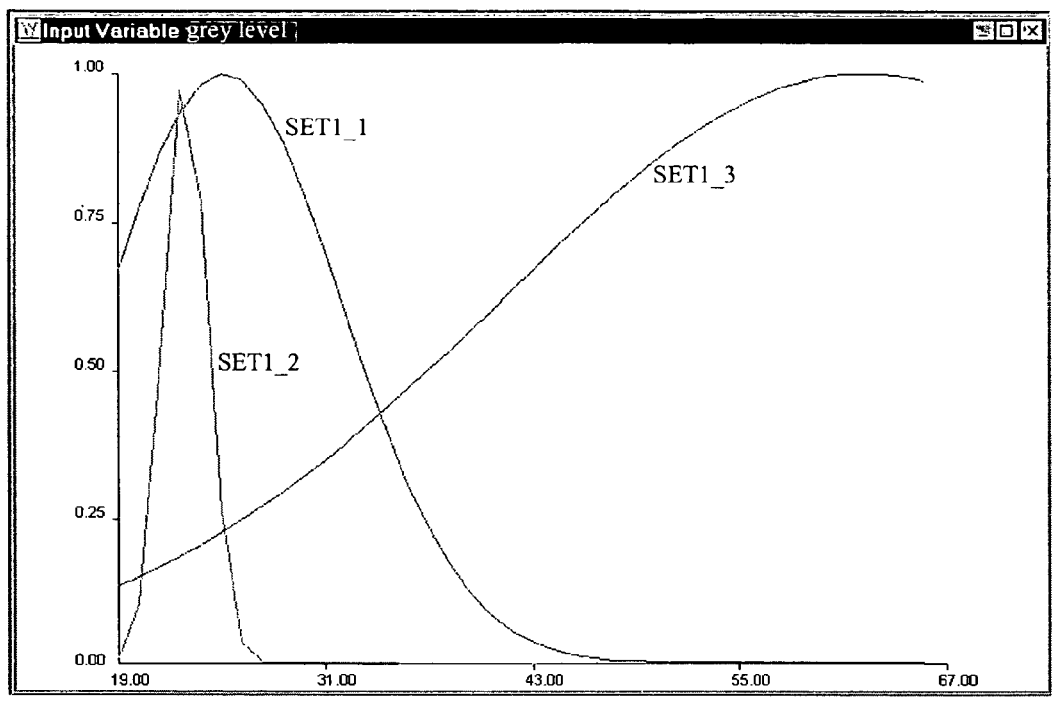
FIG. 28 is a diagram of member functions used in the fuzzy logic algorithm of this invention relative to the grey level of a pixel.
Figure 29:
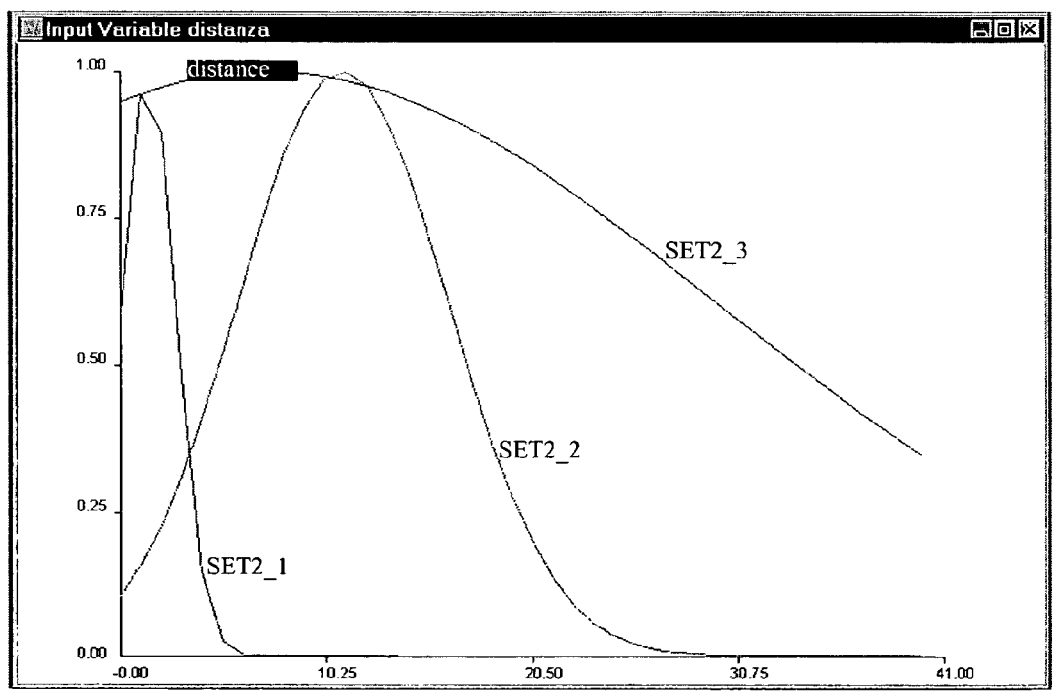
FIG. 29 is a diagram of member functions used in the fuzzy logic algorithm of this invention relative to the distance between the grey level of a pixel and the mean value of grey level of the respective background pixels.
Figure 30:
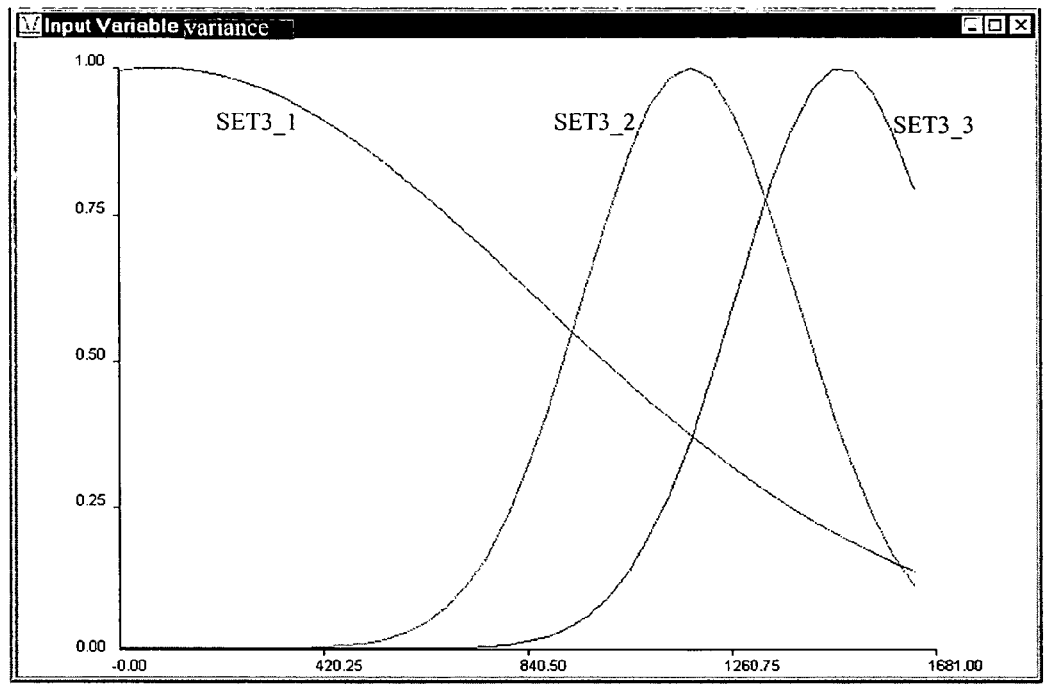
FIG. 30 is a diagram of member function used in the fuzzy logic algorithm of this invention relative to the square of the distance between the grey level of a pixel and the mean value of grey level of the respective background pixels.

An output simulation diagram generated by the fuzzy logic algorithm for the training patterns of two spots with far different grey level distributions is shown in FIG. 27.

Figures from 28 to 30 show the membership functions of the input variables of the fuzzy logic algorithm, respectively of the grey level, of the distance $\delta$ and of the square of the distance $\delta^2$.

Figure 31:
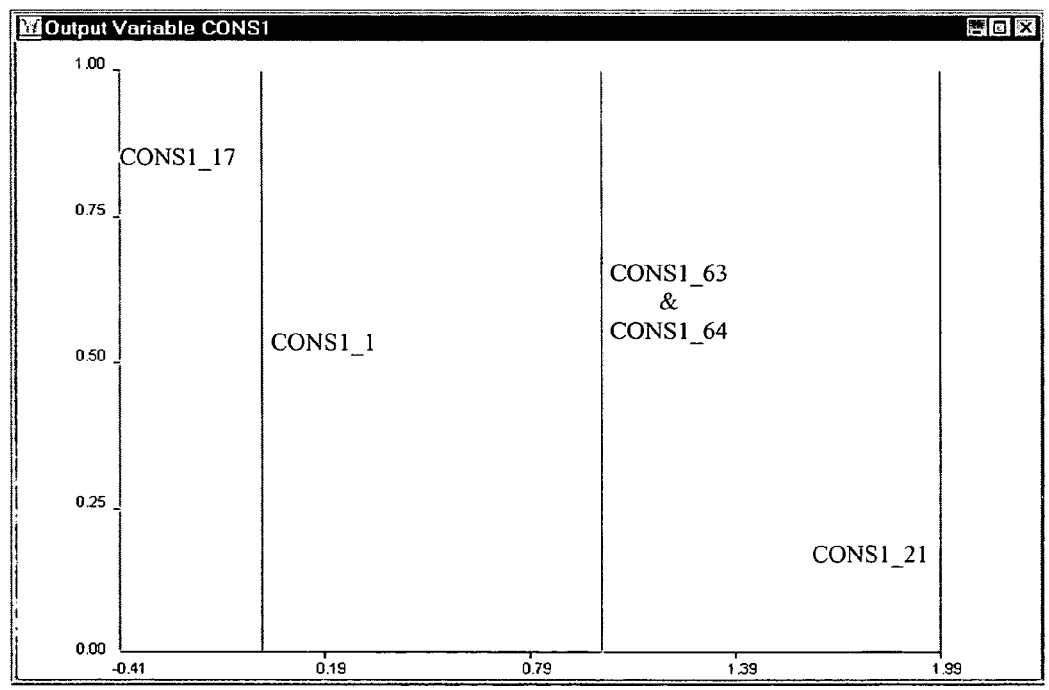
FIG. 31 is a diagram of the consequents of the fuzzy logic algorithm of this invention.

The consequents of the fuzzy algorithm are reported in FIG. 31. More details on the fuzzy logic predicate of the segmentation algorithm (intra-spot segmentation) of this invention are reported hereinbelow.

---

FUZZY SYSTEM WITH GAUSSIAN MEMBER FUNCTION

Formula of the member function (shape):

$$y = \exp\left(-\frac{(x - m)^2}{2s^2}\right)$$

wherein:
x is the input value;
m is the mean;
s is the standard deviation.
Hereinafter this function is called GAUSS(x, m, s).

* Input variables *

Input variable 1: gray level
Fuzzy Set Name:                                     Centroid:
SET1_1 25.182846
Shape: GAUSS($x_1$, 25.182846, 9.731716)
Fuzzy Set Name:                                     Centroid:
SET1_2 22.915066
Shape: GAUSS($x_1$, 22.915066, 1.789337)

-continued

FUZZY SYSTEM WITH GAUSSIAN MEMBER FUNCTION

Fuzzy Set Name: SET1_3 62.334343    Centroid:
Shape: GAUSS($x_1$, 62.334343, 30.384819)
Input variable 2: distance
Fuzzy Set Name: SET2_1 1.411060    Centroid:
Shape: GAUSS($x_2$, 1.411060, 1.927289)
Fuzzy Set Name: SET2_2 11.101624    Centroid:
Shape: GAUSS($x_2$, 11.101624, 7.363041)
Fuzzy Set Name: SET2_3 7.3 16561    Centroid:
Shape: GAUSS($x_2$, 7.316561, 31.509554)
Input variable 3: square of the distance
Fuzzy Set Name: SET3_1 88.555168    Centroid:
Shape: GAUSS($x_3$, 88.555168, 1090.161377)
Fuzzy Set Name: SET3_2 1176.142700    Centroid:
Shape: GAUSS($x_3$, 1176.142700, 310.110229)
Fuzzy Set Name: SET3_3 1488.746460    Centroid:
Shape: GAUSS($x_3$, 1488.746460, 308.677734)
                    * Output variables *

Output variables 1: CONS1
Fuzzy Set Names:    Centroids:
CONS1_1             0.006696
CONS1_17            −0.413813
CONS1_21            1.986579
CONS1_63            1.001855
CONS1_64            0.999214

The fuzzy logic criterion described above may be conveniently used for performing the GENERAL CLUSTERING step of the algorithm disclosed in the document "A NEW CLUSTERING BASED SYSTEM FOR AUTOMATED OBJECT RECOGNITION" SOCO 198—University of Catania, by Enrico Alessi, Salvatore Coco, Giuseppe Pappalardo, Giacomo Capizzi, for carrying out the segmentation operation.

According to a preferred embodiment of the method of analyzing array images, the intra-spot segmentation operation is carried out through the processing steps illustrated schematically in FIG. 14, using the above described fuzzy logic criterion instead of a threshold criterion, that has so far been used for isolating the single spots.

A system for carrying out the intra-spot segmentation may be as the one illustrated in FIG. 26 and described with reference to the spot extraction operation.

In this case though, the block FEATURES EXTRACTION determines for each scanned pixel the respective three antecedents of the fuzzy logic algorithm (grey level $\delta$, $\delta^2$) and provides this information to the block CLUSTERING CONDITION which groups the pixels in elementary clusters by applying the fuzzy logic criterion. The block CLUSTERING carries out the other steps of the algorithm as already described above.

The output clusters: CLUSTER 1, ..., CLUSTER N; represent in this case objects (constituted by signal pixels) identified within the analyzed spot.

Once the intra-spot segmentation operation is completed, each single spot of the array is finally examined for generating characteristic parameters and quality indexes. These parameters allow us to characterize a spot and eventually carry out a comparative analysis between images obtained for different dyes (for example Cy3 and Cy5) used for rendering evident the hybridization of DNA samples.

The following table illustrates several useful parameters for characterizing a spot and the manner in which they are calculated, making reference to the cited figure.

TABLE 1

Figure 32:
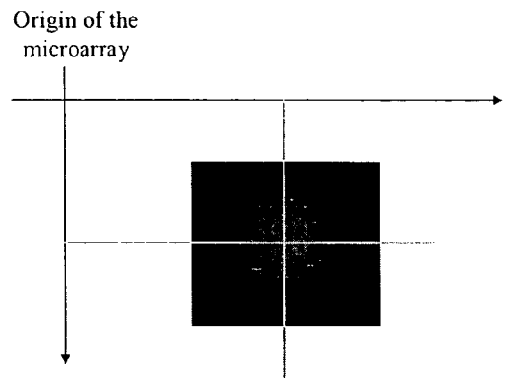
FIGS. 32 to 40 show how to calculate characteristic parameters and quality indexes of spots isolated by the method of this invention.
Figure 33:
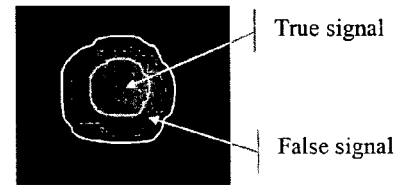
Figure 34:
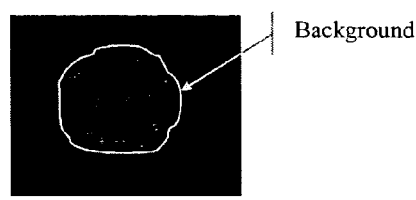
Figure 35:
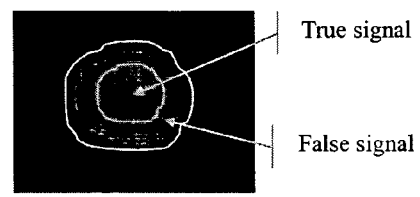
Figure 36:
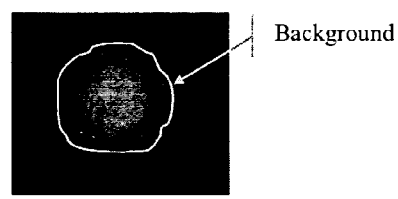
Figure 37:
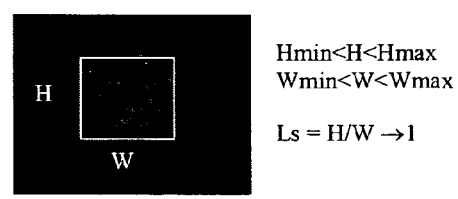
Figure 38:
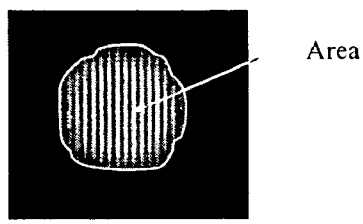
Figure 39:
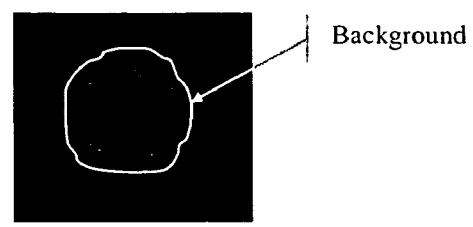
Figure 40:
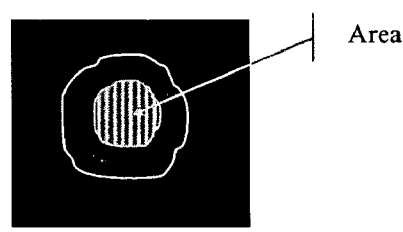

| Parameter | Meaning |
| --- | --- |
| Center of the spot | Coordinates of the center of gravity of the spot - FIG. 32 |
| Mean of the signal | Mean of the grey levels of the pixels of the spot belonging to the class True signal - FIG. 33 |
| Mean of the background | Mean of the grey levels of the pixels of the spot belonging to the perimeter of the spot's shape - FIG. 34 |
| Median of the signal | Median of the grey levels of the pixels of the spot belonging to the class True signal - FIG. 35 |
| Median of the background | Median of the grey levels of the pixels of the spot belonging to the shape's perimeter - FIG. 36 |
| FOMV | Mean of the output of the fuzzy system for the pixels attributed to the class True signal |
| Symmetry factor | Ratio between height and width of the minimum rectangle that inscribe the spot - FIG. 37 |
| Area of the spot | Number of pixels of the spot - FIG. 38 |
| Area of background | Number of pixels of the shape's perimeter - FIG. 39 |
| Area of signal | Number of pixels belonging to the class True signal - FIG. 40 |
| Correction factor | Difference between the median of the grey levels of the pixels of the signal and the median of the grey levels of the pixels of background |

An important parameter for evaluating the quality of the extracted spot is that indicated with the acronym FOMV, given by the mean of output of the fuzzy system for the signal pixels, which is an index of the quality of the discrimination of the signal pixels from the background pixels. The more the fuzzy output approximates 1, the more reliable may be considered the identification of a pixel as a signal pixel and not as a background pixel. By making a mean of the fuzzy output, a quality index of the selection of the signal pixel from the background pixels is obtained.

The method of this invention for the identification of pixels belonging to a same cluster (object) from background pixels is per se useful also for analyzing within an image of any kind, that is images other than those acquired from a DNA chip.

Accordingly, the pixels of an image to be analyzed are scanned and using a fuzzy logic algorithm, a characteristic value for each scanned pixel is calculated: if such a characteristic value exceeds a preset threshold, the pixel is regarded as belonging to an object (cluster) identified on the more or less local background of the image.

The choice of antecedents used in the fuzzy logic algorithm will be made after having studied the histogram of the grey levels of the image.

As for the case of performing an intra-spot segmentation in analyzing array images described above, the following three antecedents for an effective fuzzy logic algorithm will be chosen:
 i) the grey level of the single pixel under scrutiny;
 ii) the distance ($\delta$) of the grey level of the pixel under scrutiny from the mean grey level of background pixels; and
 iii) the square of the above defined distance ($\delta^2$).

Substantially, the method of object recognition of this invention comprises in scanning the pixels of the image, calculating a characteristic value for each pixel using a fuzzy logic algorithm, the antecedents of which are those specified above and comprise of course the operations of calculating the mean value of the grey level of background pixels preferably in an area immediately surrounding the object to be identified and of selecting the scanned pixels as belonging to a same object if their respective characteristic value exceeds a preset threshold.

Preferably, each antecedent has three membership functions, each being a Gaussian function of predetermined mean and variance.

The fuzzy logic criteria may be the same as reported above in relation to the sample illustrations of FIGS. 28 to 31.

The flow chart of this method of identification of pixels of an image belonging to a same object will be similar to that (already described) of FIG. 14.

A possible system of identification embodying this method has been already described in relation to FIG. 26.

The method of identification of this invention may even be conveniently used for carrying out the intra-spot segmentation of spots of array images independently on the particular technique used for locating and isolating the single spots.

Although exemplary embodiments of the method and apparatus of the present invention have been illustrated in the accompanying Drawings an described in the foregoing Detailed Description, it is understood that the invention is not limited to the embodiments disclosed, but is capable of numerous rearrangements, modifications, and substitutions without departing from the spirit of the invention as set forth and defined by the following claims:

What is claimed:

1. A method of analysis of an array image including one or more luminous spots on a background, comprising:
    operating an array localization system implementing morphological filtering by:
        determining a shape and location of each spot on the array image;
        generating a binary map of pixels defining a boundary of each spot on the background;
        isolating each spot from the background by an extraction operation using said binary map;
        examining each spot by a segmentation operation to identify pixels belonging to a same cluster according to a preestablished criterion; and
        for each spot, defining relative characteristic parameters and quality indexes determined in function of gray levels of pixels of the spot;
    wherein generating said binary map comprises:
        filtering the array image with at least a morphological filter generating only a single corresponding marker image of the background;
        determining a background level by carrying out a reconstruction operation on said single corresponding marker image to generate a corresponding reconstructed image of the background;
        generating a filtered image from which the luminosity of the background is removed by performing a top-hat operation on said reconstructed background image and the array image; and
        performing a thresholding operation on said filtered image of the background luminosity.

2. The method of claim 1, wherein said reconstruction operation is carried out using circular masks.

3. The method of claim 2, further comprising filtering the noise corrupting said binary map by:
    carrying out in succession two erosion operations using circular masks of different ratios;
    carrying out a dilation operation using a circular mask of diameter larger than the maximum dimensions of the spot,
    generating a binary map filtered from noise; and
    using said binary map filtered from noise in said extraction operation.

4. The method of claim 1, wherein said marker image is generated by:
    defining on a Cartesian reference frame spots present in the array image;
    carrying out in succession the following morphological filtering operations of said spots with directional openings having as structuring sets segments of length not larger than the maximum dimension of the spots and oriented, respectively, along:
        the bisecting line of the first and third quadrant;
        the bisecting line of the second and fourth quadrant;
        the abscissa axis; and
        the ordinate axis; of said Cartesian reference frame.

5. The method according to claim 1, wherein said extraction operation comprises:
    scanning pixels of an image by column or by row, associating to adjacent pixels scanned in succession and corresponding to pixels of the relative binary map having the same logic active value a quadruplet defining an elementary cluster composed of an identification number, minimum and maximum coordinates and number of column or of row;
    identifying for each elementary cluster in a certain column or row a set of elementary clusters in the column or row immediately preceding bordering said elementary cluster;
    identifying in said set of elementary cluster a winner cluster having the largest number of boundary pixels with said elementary cluster and the remaining clusters as losers, and making the identification number of said elementary cluster equal to the identification number of said winner cluster;
    making the identification number of each of the loser clusters equal to the identification number of the respective winner cluster; and
    selecting pixels of luminous spots by extracting from the original image pixels of clusters having the same identification number.

6. The method of claim 1, wherein said preestablished criterion of segmentation comprises calculating a characteristic value for pixels of a spot by a fuzzy logic algorithm in order to discriminate pixels belonging to foreground and to background, wherein calculating comprises:
    calculating for said spot the mean value of grey level of the background pixels, said fuzzy logic algorithm using as antecedents:
        the grey level of a pixel;
        the distance between said grey level of the pixels and the mean grey level of the background pixels; and
        the square of said distance; and
    recognizing said pixels as belonging to a same cluster if said characteristic value exceeds a preestablished threshold.

7. The method of claim 6, further comprising: defining by said preset criterion for each spot a first zone containing signal pixels and a second zone containing background and/or noise pixels.

8. The method of claim 6, wherein each antecedent has three distributed membership functions.

9. The method of claim 8, wherein said membership functions are Gaussian distributed membership functions having preset mean and variance.

10. The method of claim 6, wherein said fuzzy logic algorithm has five consequents.

11. The method of claim 6, wherein said segmentation operation comprises:

scanning pixels of an image by column or by row, associating to adjacent pixels scanned in succession and corresponding to pixels of the relative binary map having the same logic active value a quadruplet defining an elementary cluster composed of an identification number, minimum and maximum coordinates and number of column or of row;

identifying for each elementary cluster in a certain column or row a set of elementary clusters in the column or row immediately preceding bordering said elementary cluster;

identifying in said set of elementary cluster a winner cluster having the largest number of boundary pixels with said elementary cluster and the remaining clusters as losers, and making the identification number of said elementary cluster equal to the identification number of said winner cluster;

making the identification number of each of the loser clusters equal to the identification number of the respective winner cluster; and selecting pixels of luminous spots by extracting from the original image pixels of clusters having the same identification number.

12. The method of claim 7 comprising calculating for each spot characteristic parameters and quality indexes belonging to the group consisting of the mean value of the grey levels of the pixels of said first zone;

the coordinates of the center of gravity of the spot;

the mean value of the grey levels of the border pixels of the spot;

the median of the grey levels of said first zone;

the median of the grey levels of said border pixels of the spot;

the ratio between height and width of the smallest rectangle containing said first zone;

the number of pixels composing the spot;

the number of border pixels of the spot;

the number of pixels of said first zone;

a normalization factor of the grey levels of the pixels equal to the difference between the median of the grey levels of the pixels of said first zone and the median of the grey levels of the border pixels of the spot; and the mean value of said characteristic value for the pixels of said first zone.

13. A device for the analysis of array images comprising:

an array localization system having the architecture of a cellular neural network for processing the pixels of luminous spots and implementing morphological filtering by:

determining a shape and location of each spot on the array image;

generating a binary map of pixels defining a boundary of each spot on the dark background;

isolating each spot from the background by an extraction operation using said binary map;

examining each spot by a segmentation operation to identify pixels belonging to a same cluster according to a preestablished criterion; and for each spot, defining relative characteristic parameters and quality indexes;

wherein generating said binary map comprises:

i) filtering the array image with at least a morphological filter generating only a single corresponding marker image of the background;

ii) determining a background level by carrying out a reconstruction operation on said single corresponding marker image to generate a corresponding reconstructed image of the background;

iii) generating a filtered image from which the luminosity of the background is removed by performing a top-hat operation on said reconstructed background image and the array image; and iv) performing a thresholding operation on said filtered image of the background luminosity.

14. The device of claim 13, having a spot extraction system for isolating luminous spots on a background of an array image, comprising:

a scanning subsystem of the pixels of an image;

a subsystem of identification of elementary clusters composed of adjacent pixels scanned in succession implementing the spot extraction operation; and a subsystem of processing of said elementary clusters outputting clusters of pixels present in the spot.

15. The device of claim 14, having an intra-spot segmentation system of luminous spots on a background of an image, comprising:

a scanning subsystem of pixels of a spot; and a fuzzy logic processing subsystem coupled to said scanning subsystem, the subsystem discriminating the scanned pixels in foreground signal pixels and background or noise pixels using fuzzy logic processing using Gaussian distributed membership functions.

16. The device of claim 15, wherein said fuzzy logic processing subsystem implements an intra-spot segmentation operation and comprises:

a subsystem defining elementary clusters composed of adjacent pixels, and further comprising a processing subsystem of said elementary cluster that outputs clusters of pixels found in said spot.

* * * * *